US00PP32567P2

(12) United States Plant Patent
Scheys

(10) Patent No.: US PP32,567 P2
(45) Date of Patent: Dec. 1, 2020

(54) ***HEUCHERA* PLANT NAMED 'HAPPY MOON'**

(50) Latin Name: ***Heuchera* hybrid**
Varietal Denomination: Happy Moon

(71) Applicant: Diederik Alexander Maria Scheys, Réty (FR)

(72) Inventor: Diederik Alexander Maria Scheys, Réty (FR)

( * ) Notice: Subject to any disclaimer, the term of this patent is extended or adjusted under 35 U.S.C. 154(b) by 0 days.

(21) Appl. No.: 16/602,535

(22) Filed: Oct. 24, 2019

(51) Int. Cl.
*A01H 5/12* (2018.01)
*A01H 6/80* (2018.01)

(52) U.S. Cl.
USPC ..... Plt./440

(58) Field of Classification Search
USPC ..... Plt./440, 250, 311, 413
CPC ... A01H 5/12; A01H 5/02; A01H 5/00; A01H 6/80; A01H 6/14
See application file for complete search history.

(56) References Cited

PUBLICATIONS

Journees des Plantes de Chantilly 2017, retrieved on Apr. 16, 2020, retrieved from the Internet at https://www.domainedechantilly.com/wp-content/uploads/2019/06/DP2-Aut2017-7.pdf, pp. 3 and 14-18. (Year: 2017).*
Google English translation for Journees des Plantes de Chantilly, retrieved on Apr. 16, 2020, retrieved from the Internet at https://www.google.com/search?q=google+translation&rlz=101GCEB_enUS773US773&oq=google+translation&aqs=chrome..69i57j017.4703j0j1&sourceid=chrome&ie=UTF-8, 2 pp. (Year: 2020).*

* cited by examiner

*Primary Examiner* — June Hwu
(74) *Attorney, Agent, or Firm* — Penny J. Aguirre

(57) ABSTRACT

A new cultivar of *Heuchera* plant named 'Happy Moon' that is characterized by its leaves that are pale green to green-yellow in color with red veins with the red veins more prominent in spring, its tolerance to high sunlight, its vigorous growth habit, its dense, mounded plant habit and its small flowers that are held on upright flowering stems.

2 Drawing Sheets

Botanical classification: *Heuchera* hybrid.
Cultivar designation: 'Happy Moon'.

CROSS REFERENCE TO RELATED APPLICATIONS

This application is related to a European plant breeders' rights application filed on Dec. 19, 2017, application No. 2017/3331. There have been no offers for sale anywhere in the world prior to the effective filing date of this Application and no accessibility to one of ordinary skill in the art could have been derived from the printed plant breeder's rights documents. This application is co-pending with a U.S. Plant Patent Application filed for a plant derived from the same breeding program that is entitled *Heuchera* Plant Named 'Happy Flames' (U.S. Plant patent application Ser. No. 16/602,544).

BACKGROUND OF THE INVENTION

The present invention relates to a new and distinct cultivar of *Heuchera* of hybrid origin, botanically known as *Heuchera* 'Happy Moon' and is hereinafter referred to by its cultivar name 'Happy Moon'.

The new cultivar was discovered as a chance seedling in a container by the Inventor in Réty, France in July of 2015. The source of the seedling was from seed collected in 2008 from open pollinated plants in a trial field that contained numerous proprietary *Heuchera* seedlings from the Inventor's breeding program and other cultivars. The parentage of 'Happy Moon' is therefore unknown.

Asexual propagation of the new cultivar was first accomplished under the direction of the Inventor by tissue culture initiated from meristem tissue in June of 2018 in Beervelde, Belgium. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Happy Moon' as a new and unique cultivar of *Heuchera*.

1. 'Happy Moon' exhibits leaves that are pale green to green-yellow in color with red veins with the red veins more prominent in spring.
2. 'Happy Moon' exhibits tolerance to high sunlight.
3. 'Happy Moon' exhibits a vigorous growth habit.
4. 'Happy Moon' exhibits a dense, mounded plant habit.
5. 'Happy Moon' exhibits small flowers that are held on upright flowering stems.

'Happy Moon' can be most closely compared to the *Heuchera* cultivars 'Delta Dawn' (U.S. Plant Pat. No. 23,545), 'Red Lightning' (U.S. Plant Pat. No. 27,767), and 'Happy Flames'. All three are similar to 'Happy Moon' in foliage coloration. 'Delta Dawn' differs from 'Happy Moon' in having a less dense plant habit, leaves that are darker in color, flower stems that are shorter in length and more similar to typical *Heuchera villosa* hybrids, whereas the flower stems of 'Happy Moon' are more similar to typical

*Heuchera sanguinea* hybrids. 'Red Lightning' differs from 'Happy Moon' in having a less dense plant habit, leaves that are darker in color and larger in size, and flower stems that are shorter in length. 'Happy Flames' differs from 'Happy Moon' in having a foliage that is darker green and less yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website disclosures by Pioneer Seeds, RHS Gardening, Denis plants, and Pépiniére des DEUX CAPS.

BRIEF DESCRIPTION OF THE DRAWINGS

The accompanying colored photograph illustrates the overall appearance and distinct characteristics of the new *Heuchera*. The photograph was taken of a plant 18 months in age as grown outdoors in a 9-cm container in Attenhove, Belgium.

The photograph in FIG. 1 provides a side view of the plant of 'Happy Moon' in bloom.

Figure 1:
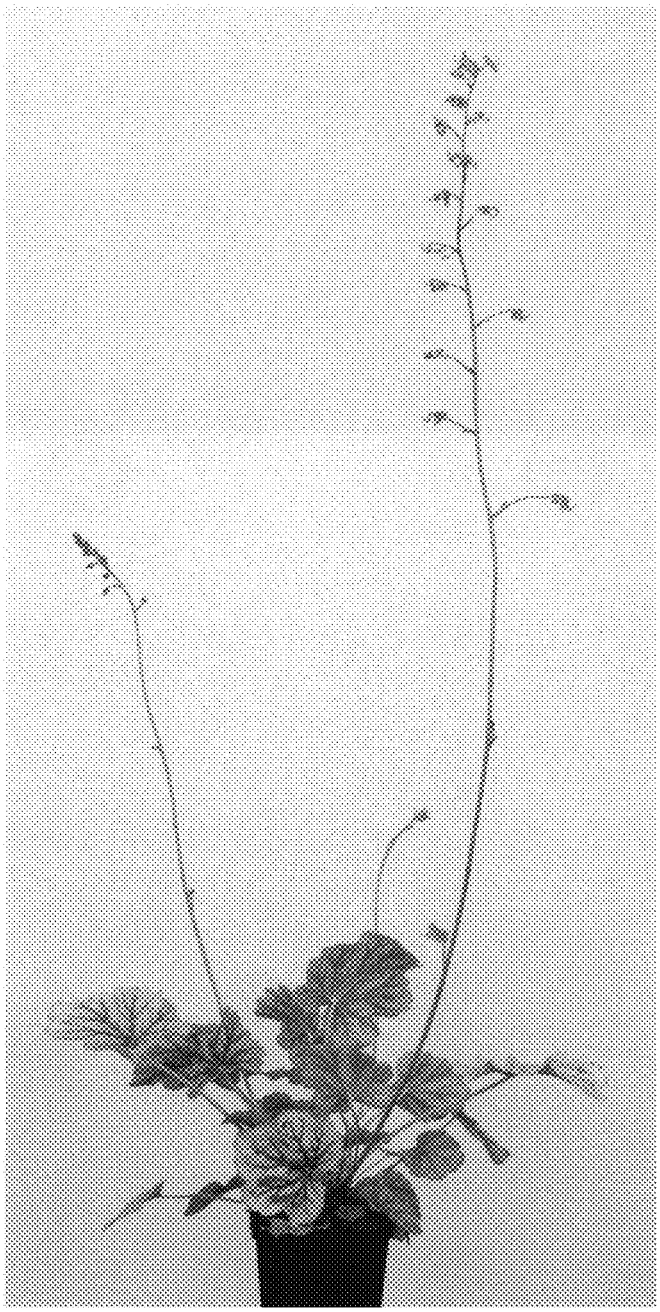
Figure 2:
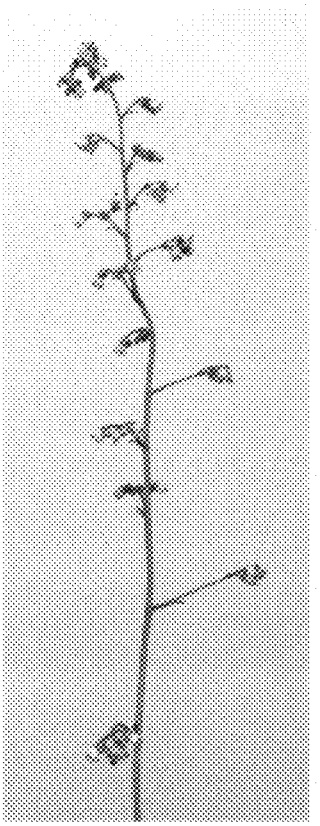

The photograph in FIG. 2 provides a close up of the inflorescence of 'Happy Moon'.

Figure 3:
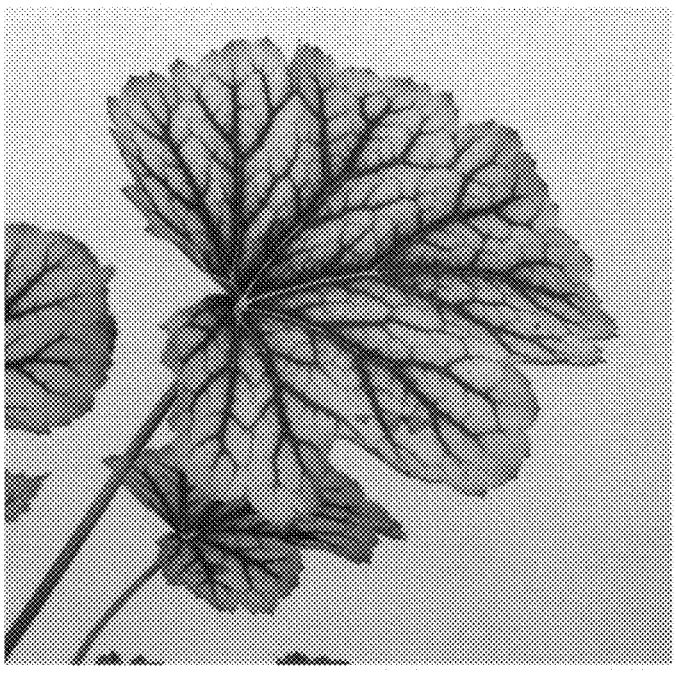

The photograph in FIG. 3 provides a close up of a mature leaf of 'Happy Moon'.

The colors in the photograph are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 9-cm containers in Attenhove, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring into summer in Belgium.

*Plant type.*—Herbaceous perennial, leaves emerge from rootstock (stemless).

*Plant habit.*—Dense and mounded with inflorescences held upright above the foliage.

*Height and spread.*—An average of 19.4 cm in height (soil level to top of foliar plane), average of 72.6 cm in height (soil level to top of floral plane) and 35.4 cm in spread.

*Hardiness.*—At least in U.S.D.A. Zones 3 to 9.

*Environmental stress.*—Tolerant to high sunlight.

*Diseases and pests.*—No susceptibility or resistance to pests or diseases has been observed.

*Root description.*—Fibrous roots on woody rootstalks, 158D in color.

*Propagation.*—Tissue culture.

*Root development.*—An average of 8 weeks to fully develop from a tissue culture plug in a 7-cm when planted April through August in Belgium.

*Growth rate.*—Vigorous.

Foliage description:

*Leaf shape.*—Broad ovate to near orbicular.

*Leaf division.*—Simple.

*Leaf base.*—Hastate, lobes free.

*Leaf apex.*—Short and abruptly acute.

*Leaf venation.*—Laciniate, upper surface 150A to 150B, lower surface 150B to 150C.

*Leaf margins.*—Crenate (shallow depth) with abruptly acute tips on each tooth, undulation very weak to weak.

*Leaf attachment.*—Petiolate.

*Leaf arrangement.*—Alternate in basal rosettes.

*Leaf lobes.*—Lobed, an average of 7 lobes, occasionally 9, shallow in depth, divergent.

*Leaf surface.*—Both surfaces non-rugose, smooth and pubescent, moderately to densely covered with very short strigose hairs an average of 0.2 mm in length and too small to measure color, upper surface very slightly glossy, lower surface matte.

*Leaf color.*—Young upper surface; 150A to 150B, area surrounding veins 173A and 176B, young lower surface; 150B, changing to 149A toward the margins, area around veins 177D, mature upper surface; 150C, changing to 10C at the margins, area around veins 174B and 177C to 177D, mature lower surface; 150C, changing to 10B to 10C at the margins, area around veins 177D, fall and winter color similar to mature foliage until browning.

*Leaf size.*—An average of 9.3 cm in length and 9 cm in width.

*Leaf quantity.*—An average of 14 per basal rosette.

*Petioles.*—An average of 14.4 cm in length and 2 mm in diameter, moderate strength, surface color 144B, densely covered with very short strigose hairs, average of 1 mm in length, NN155D in color.

*Stipules.*—Leafy stipule at the base of each leaf, average length 1.6 cm, average width 4.5 mm, acute tip, color; 182A to 182B, apex 145B to 145C.

Flower description:

*Inflorescence type.*—Numerous small bell-shaped flowers arranged on panicles on peduncles emerging from a basal rosette.

*Inflorescence size.*—An average of 28 cm in height and 8.2 cm in diameter.

*Inflorescence number.*—An average of 3.

*Inflorescence density of flowers.*—Sparse.

*Flower fragrance.*—None.

*Flower quantity.*—Average of 120 flowers per flowering stem.

*Flower lastingness.*—Average of one week.

*Flower buds.*—Obovate in shape, an average of 4 mm in length and 2.5 mm in diameter, color; 145A, changing to 179A at the top, surface is matte and densely covered with very short glandular hairs; an average of 0.2 mm in length and too small to measure color.

*Flower aspect.*—Outward and nodding.

*Flower type.*—Single, campanulate.

*Flower size.*—Average of 7 mm in diameter and 6 mm in length.

*Petals.*—Average of 5, rotate arrangement and implanted in the hypanthium at base, oblanceolate in shape, margin is entire, apex is acute, base is narrow attenuate, upper and lower surface is glabrous, smooth and matte, an average of 3.5 mm in length and 0.8 mm in width, when opening upper and lower surface color; between 69D and N155B, fully open upper and lower surface color; between N155B and NN155D.

*Calyx.*—Campanulate, sepals fused to hypanthium, 6 mm in length and 5 mm in diameter.

*Sepals.*—An average of 5, lower 50% fused into campanulate hypanthium, short oblong in shape, an average of 5 mm in length and 2 mm in width, margin is entire and fused into hypanthium, apex is obtuse, color; when opening and fully open upper and lower surface 155C, changing to 145B at the base, apex is 145C to 145D and 179B, both surfaces are matte and densely covered with very short glandular hairs an average of 0.2 mm in length and to small to measure color.

*Peduncle.*—An average of 74 cm in length and 2 mm in diameter, 144A to 144B in color, primary flower aspect 50°, secondary peduncle aspect to main peduncle 60°, moderate in strength, surface moderately glossy and densely covered with very short soft glandular hairs; average of 0.2 mm in length and too small to measure color.

*Pedicels.*—An average of 2 mm in length and 0.5 mm in diameter, 151B in color, primary flower aspect straight on top of secondary pedicel, secondary and tertiary flower aspect is 30°, moderate in strength, surface matte and densely covered with very short soft glandular hairs; average of 0.2 mm in length and to small too measure color.

Reproductive organs:

*Gynoecium.*—Pistils; 2, 3.5 mm in length, stigma; club-shaped, 155C in color, 0.2 mm in diameter, style; an average of 3.8 mm in length and 155C in color, ovary; 150D in color.

*Androecium.*—Stamens; 5, anthers; triangular in shape, average of 0.3 mm in length and width, 174A in color, filament; 2 mm in length and NN155D in color, pollen; none detected.

*Seed/fruit.*—No fruit or seeds have been observed to date.

It is claimed:

1. A new and distinct cultivar of *Heuchera* plant named 'Happy Moon' as herein illustrated and described.

* * * * *